(12) United States Patent
Tsujii et al.

(10) Patent No.: US 9,341,554 B2
(45) Date of Patent: May 17, 2016

(54) HARDNESS TESTER

(71) Applicant: MITUTOYO CORPORATION, Kanagawa (JP)

(72) Inventors: Masaharu Tsujii, Kanagawa (JP); Satoko Mori, Kanagawa (JP)

(73) Assignee: MITUTOYO CORPORATION, Kanagawa (JP)

( * ) Notice: Subject to any disclaimer, the term of this patent is extended or adjusted under 35 U.S.C. 154(b) by 233 days.

(21) Appl. No.: 14/193,403

(22) Filed: Feb. 28, 2014

(65) Prior Publication Data
US 2014/0250989 A1    Sep. 11, 2014

(30) Foreign Application Priority Data

Mar. 6, 2013    (JP) .................................. 2013-043714

(51) Int. Cl.
*G01N 3/42*    (2006.01)

(52) U.S. Cl.
CPC .......... *G01N 3/42* (2013.01); *G01N 2203/0078* (2013.01); *G01N 2203/0222* (2013.01)

(58) Field of Classification Search
CPC ............ G01N 3/42; G01N 2203/0222; G01N 2203/0078
USPC ............................................................. 73/81
See application file for complete search history.

(56) References Cited

U.S. PATENT DOCUMENTS

| 6,146,013 | A  | * | 11/2000 | Huetter | .............. | G01N 25/4866 |
|---|---|---|---|---|---|---|
| | | | | | | 374/10 |
| 6,279,388 | B1 | * | 8/2001 | Tsujii | ....................... | G01N 3/42 |
| | | | | | | 73/82 |
| 7,121,136 | B2 | * | 10/2006 | Tsujii | ....................... | G01N 3/42 |
| | | | | | | 73/78 |
| 8,087,282 | B2 | | 1/2012 | Sawa et al. | | |
| 8,578,284 | B2 | * | 11/2013 | Takemura | ................ | G01N 3/42 |
| | | | | | | 715/764 |
| 8,631,687 | B2 | * | 1/2014 | Patten | ...................... | G01N 3/42 |
| | | | | | | 73/81 |
| 9,046,456 | B2 | * | 6/2015 | Furuta | ....................... | G01N 3/44 |
| 2009/0044609 | A1 | * | 2/2009 | Sawa | ....................... | G01N 3/42 |
| | | | | | | 73/81 |
| 2011/0252874 | A1 | * | 10/2011 | Patten | ...................... | G01N 3/42 |
| | | | | | | 73/81 |

FOREIGN PATENT DOCUMENTS

JP    4942579    3/2012

* cited by examiner

*Primary Examiner* — Freddie Kirkland, III (74) *Attorney, Agent, or Firm* — Greenblum & Bernstein, P.L.C.

(57) ABSTRACT

A hardness tester has a test force applier generating a test force using an electromagnetic force generated by supplying a current to a drive coil provided in a magnetic field and applies the test force to an indenter to press the indenter into a surface of a sample; a temperature detector detecting a temperature of the test force applier; and a test force corrector correcting the test force generated from the test force applier based on the temperature detected by the temperature detector.

3 Claims, 5 Drawing Sheets

Test force N [kgf]　／T

| Temperature | Test force reduction rate |
|---|---|
| 20°C | 0% |
| 22°C | 2% |
| 24°C | 2.5% |
| ⋮ | ⋮ |

HARDNESS TESTER

CROSS-REFERENCE TO RELATED APPLICATIONS

The present application claims priority under 35 U.S.C. §119 of Japanese Application No. 2013-043714 filed on Mar. 6, 2013, the disclosure of which is expressly incorporated by reference herein in its entirety.

BACKGROUND OF THE INVENTION

1. Field of the Invention

The present disclosure relates to a hardness tester.

2. Description of Related Art

As a material tester, a hardness tester is conventionally known in which forms an indentation by pressing an indenter column into a surface of a sample, the indenter column having an indenter on a foremost end thereof, and then measures a depth of the formed indentation (displacement amount of the indenter) with a displacement gauge. Using a relationship between the displacement amount and a test force applied to the indenter, the hardness tester measures physical property values of the sample, such as hardness.

As such a hardness tester above, a hardness tester is known in which electromagnetic force (force motor) is employed in a mechanism that applies a test force to an indenter to allow selection of a desired test force (refer to Japanese Patent No. 4942579, for example). When the electromagnetic force is employed in the mechanism that applies the test force, a lever system is employed. Thus, when the indenter is pressed into a sample, a relative position changes between a coil and a magnet in a test force applier that generates the electromagnetic force, thus leading to a reduction in magnetic flux density and thus in test force. A conventional hardness tester therefore incorporates a test force correction function to address the reduction in the test force associated with the change of the relative position between the coil and the magnet.

In the conventional hardness tester, however, current flows in the coil to generate the test force. Thus, heat cannot be prevented from being generated in the test force applier. With heat generated in the magnet of the test force applier, the magnetic flux density is reduced, and thus the test force is reduced. In particular, when a large test force (for example, 0.3 to 2 kgf) is generated, a large current (for example, 0.195 to 1.3 A) flows in the coil. Thus, excessive heat is generated in the test force applier, leading to a substantial reduction in the test force.

SUMMARY OF THE INVENTION

An advantage of the present disclosure provides a hardness tester capable of achieving highly precise test force by addressing a reduction in test force associated with heat generated in a test force applier.

In view of the above, a first aspect of the present disclosure provides a hardness tester measuring hardness of a sample by applying a test force to a surface of the sample with an indenter to form an indentation and by measuring a depth of indentation of the indenter at a time of forming the indentation. The hardness tester includes a test force applier generating the test force using an electromagnetic force generated by supplying a current to a drive coil provided in a magnetic field and applying the test force to the indenter to press the indenter into the surface of the sample; a temperature detector detecting a temperature of the test force applier; and a test force corrector correcting the test force generated from the test force applier based on the temperature detected by the temperature detector.

A second aspect of the present disclosure provides the hardness tester according to the first aspect, further including a test force measurer measuring the test force applied by the indenter to the sample placed on an upper surface; and a memory storing a test force correction table generated based on the test force generated by the test force applier, a measurement value of the test force measured by the test force measurer, and the temperature detected by the temperature detector. The test force corrector corrects the test force generated by the test force applier based on the test force correction table stored in the memory.

A third aspect of the present disclosure provides the hardness tester according to the second aspect, further including a lifting/lowering device moving the test force measurer in an up-down direction; an ingress amount detector detecting an amount of ingress of the indenter pressed into the surface of the sample by the test force applier; a determiner causing the lifting/lowering device to adjust a height of a position where the indenter comes into contact with the sample based on the amount of ingress of the indenter detected by the ingress amount detector after the indenter is pressed into the surface of the sample by the test force applier, and determining whether the height of the position where the indenter comes into contact with the sample is at a predetermined reference position; a measurement controller causing the test force measurer to measure the test force applied to the sample and causing the temperature detector to detect the temperature of the test force applier when the determiner determines that the height is at the predetermined reference position; and a table generator generating the test force correction table based on a measurement value of the test force and the detected temperature under control of the measurement controller.

According to the present disclosure, the test force can be corrected in association with a reduction in the test force due to heat generated in the test force applier, and thus highly precise test force can be achieved.

BRIEF DESCRIPTION OF THE DRAWINGS

The present disclosure is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF PREFERRED EMBODIMENTS

The particulars shown herein are by way of example and for purposes of illustrative discussion of the embodiments of the present disclosure only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description is taken with the drawings making apparent to those skilled in the art how the forms of the present invention may be embodied in practice.

An embodiment of the present disclosure is described below in detail with reference to the drawings. In the description below, an X direction is a left-right direction, a Y direction is a front-back direction, and a Z direction is an up-down direction in the drawings. Furthermore, an X-Y plane is a horizontal plane.

Figure 1:
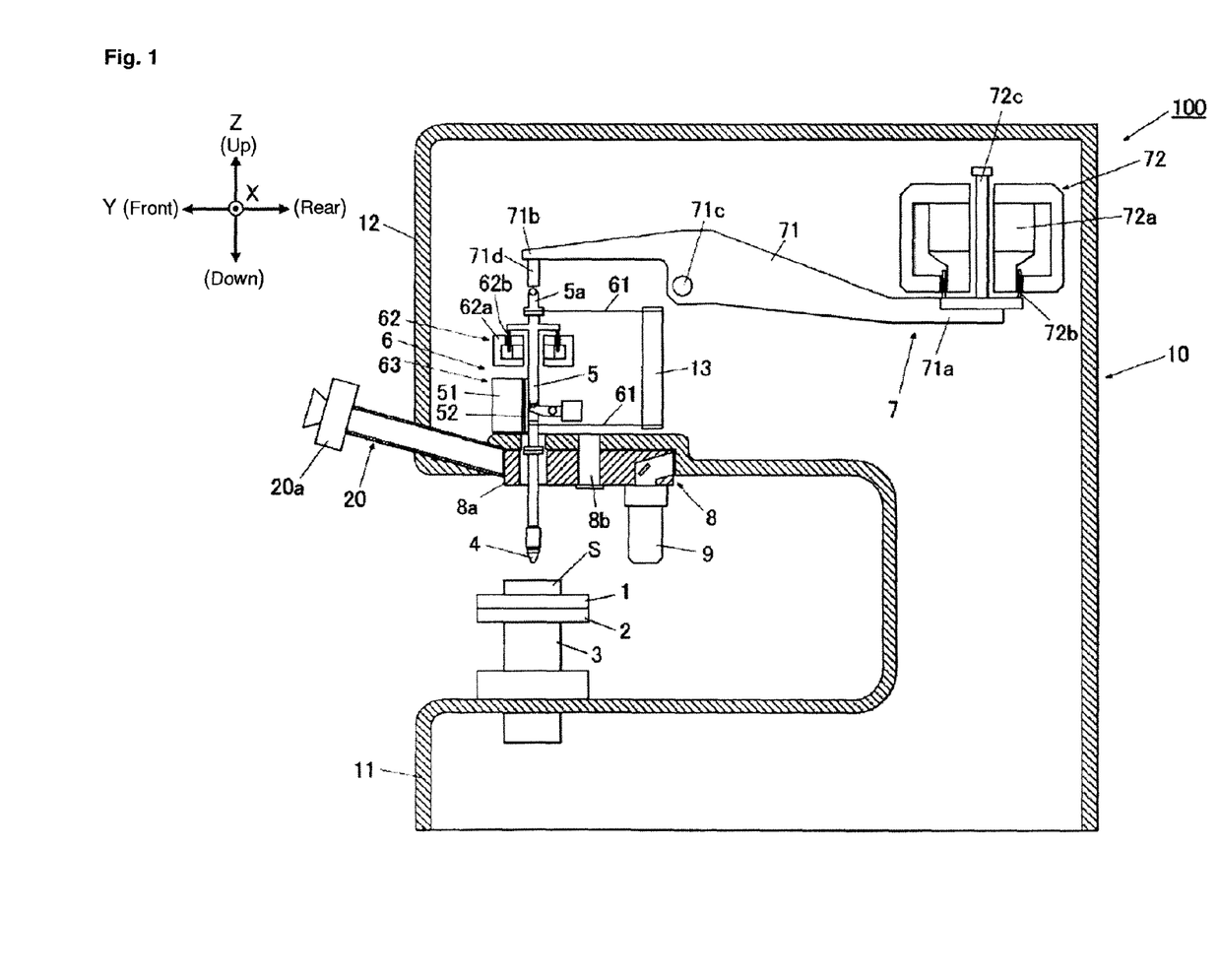
FIG. 1 is a right side view illustrating an overall configuration of a hardness tester according to an embodiment.
Figure 2:
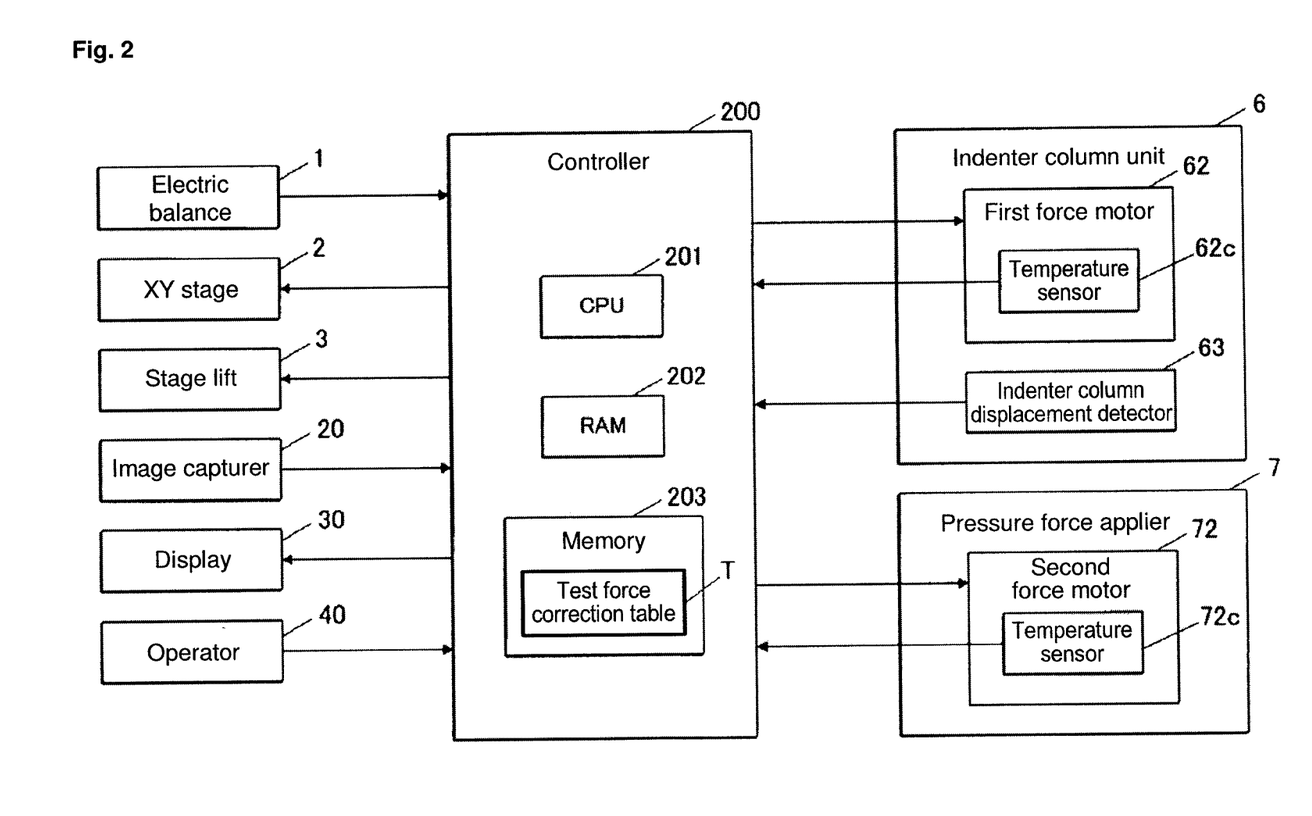
FIG. 2 is a block diagram illustrating a control configuration of the hardness tester according to the present embodiment.

With reference to FIGS. 1 and 2, a hardness tester 100 according to the present embodiment includes a tester main body 10 in which each component is provided and a controller 200 performing all-inclusive control of the tester main body 10.

The tester main body 10 has an electric balance 1, an XY stage 2, a stage lift 3, an indenter column unit 6, a pressure force applier 7, a turret 8, an objective lens 9, an image capturer 20, a display 30, an operator 40, and the like. The electric balance 1 serves as a test force measurer that measures a test force applied to a sample S placed on an upper surface. The XY stage 2 can move the electric balance 1 in the XY direction. The stage lift 3 serves as a lifting/lowering device that moves the electric balance 1 in the Z direction. The indenter column unit 6 has an indenter column 5 having at a lower end thereof an indenter 4 that forms an indentation in the sample S placed on the electric balance 1. The pressure force applier 7 applies a predetermined test force to the indenter column 5. The turret 8 allows either the indenter column 5 or the objective lens 9 to be placed over the sample S. The objective lens 9 is held to a lower surface of the turret 8. The image capturer 20 captures an image of an indentation and the like formed in a surface of the sample S.

The electric balance 1 is configured to allow the sample S to be placed on an upper surface thereof. The electric balance 1 measures a test force applied to the sample S by the indenter 4 and outputs to the controller 200 a signal based on the measured test force. The XY stage 2 is configured to allow the electric balance 1 to be placed on an upper surface thereof. The XY stage 2, which is configured to move in the XY direction (horizontal direction) in accordance with a control signal input from the controller 200, can move the electric balance 1 placed on the upper surface in the XY direction. The stage lift 3, which is provided to a lower surface of the XY stage 2, moves the XY stage 2 and the electric balance 1 in the Z direction (up-down direction) in accordance with a control signal input from the controller 200. Furthermore, the stage lift 3 is provided on an upper surface of a base 11 projecting forward below the tester main body 10. Thus, the sample S is moved in the XY direction by the XY stage 2 and in the Z direction by the stage lift 3 so as to adjust a position thereof relative to the indenter 4 or the objective lens 9.

The indenter column unit 6 is provided in an arm 12 projecting forward above the tester main body 10. The indenter column unit 6 has support springs 61; the indenter column 5; a first force motor 62; an indenter column displacement detector 63; and the like. The support springs 61 are provided in a fixed portion 13 of the arm 12. The indenter column 5 is elastically supported by the support springs 61 respectively at an upper end and a lower end. The first force motor 62 generates a test force to move the indenter column 5 in the axis direction, and thus applies the test force to the indenter column 5. The indenter column displacement detector 63 detects a displacement amount of the indenter column 5. The indenter column 5 has at the lower end thereof the indenter 4 that presses against the sample S from above to form an indentation in the surface thereof, the sample S being placed on the upper surface of the electric balance 1.

The support springs 61 are plate springs having first ends fixed to the fixed portion 13 and substantially horizontally extending from the fixed portion 13. Second ends of the plate springs 61 are connected respectively to the upper end and the lower end of the indenter column 5, thus supporting the indenter column 5 perpendicularly with respect to the electric balance 1. When the indenter column 5 is moved up and down by the first force motor 62 or the like, the support sprints 61 bend such that the indenter column 5 is held perpendicular to the electric balance 1.

The first force motor 62 includes a magnetic circuit configuration 62a, a drive coil 62b provided to the indenter column 5, and a temperature sensor 62c. In response to a control signal input from the controller 200, the first force motor 62 moves the indenter column 5 in the axis direction to apply a test force to the indenter column 5 (indenter 4). The first force motor 62 utilizes, as a driving force, a force generated by electromagnetic induction (electromagnetic force) between a magnetic field generated in a gap by a magnet in the magnetic circuit configuration 62a and an electric current flowing in the drive coil 62b positioned inside the gap. In other words, the first force motor 62 generates a desired drive force in accordance with a current amount supplied to the drive coil 62b of the first force motor 62, and, based on the drive force, applies various test forces to the indenter column 5. With the test force applied to the indenter column 5, the indenter 4 at the lower end of the indenter column 5 is pressed into the surface of the sample S. The first force motor 62 can apply the test force within a range from 10 gf (low) to 30 gf (high), for example. The temperature sensor 62c, which is provided in the vicinity of the magnet in the magnetic circuit configuration 62a, detects the temperature of the first force motor 62. The temperature sensor 62c then outputs to the controller 200 a signal based on the detected temperature. Thus, the first force motor 62 serves as a test force applier, which generates and applies the test force to the indenter 4 to press the indenter 4 into the surface of the sample S, the test force being generated by the electromagnetic force generated by supplying the current to the drive coil 62b positioned in the magnetic field. Furthermore, the temperature sensor 62c serves as a temperature detector, which detects the temperature of the first force motor 62.

The indenter column displacement detector 63 includes a scale 51 provided to the indenter column 5 and carved with calibration marks at predetermined intervals, and a linear encoder 52 optically reading the calibration marks on the scale 51. The indenter column displacement detector 63 detects an amount of displacement of the indenter column 5 when the indenter 4 is pressed into the sample S (specifically, an amount of ingress of the indenter 4 being pressed into the sample S (depth of indentation)), and then outputs to the controller 200 an indenter column displacement signal based on the detected amount of displacement. In the present embodiment, a reference position is defined in advance at a position where the indenter 4 can most effectively transmit the test force to the sample S. The reference position is specifically defined at a position of a calibration mark of 1 mm on the scale 51. Thus, the indenter column displacement detector 63 serves as an ingress amount detector, which detects the amount of ingress of the indenter 4 pressed into the surface of the sample S.

The pressure force applier 7 includes a control lever 71, a second force motor 72, and the like. The control lever 71 is provided above the indenter column unit 6. The second force motor 72 generates a test force to rotate the control lever 71, and thus applies the test force to the indenter column 5.

The control lever 71 is rotatably pivoted to the arm 12 by a rotation axis 71c in substantially a central portion. The second force motor 72 is attached to a first end portion 71a of the control lever 71. A second end portion 71b of the control lever 71 extends from the rotation axis 71c toward the indenter column unit 6 and is positioned above the indenter column 5. A second end portion 71b has a pressure portion 71d to press down the upper end 5a of the indenter column 5.

The second force motor 72 includes a magnetic circuit configuration 72a, a drive coil 72b, and a temperature sensor 72c. The second force motor 72 moves a load axis 72c in the axis direction to apply an acting force to the first end portion 71a to rotate the control lever 71. The second force motor 72 utilizes, as a driving force, a force generated by electromagnetic induction (electromagnetic force) between a magnetic field generated in a gap by a magnet in the magnetic circuit configuration 72a and an electric current flowing in the drive coil 72b positioned inside the gap. Thus, the second end portion 71b of the control lever 71 moves downward, and then the pressure portion 71d in the second end portion 71b presses down the indenter column 5 in the axis direction. Moving the indenter column 5 in the axis direction applies the test force to the indenter column 5 (indenter 4). With the test force applied to the indenter column 5, the indenter 4 at the lower end of the indenter column 5 is pressed into the surface of the sample S. The second force motor 72 can apply the test force within a range from 31 gf (low) to 200 gf (high) or a range from 201 gf (low) to 2,000 gf (high), for example. The temperature sensor 72c, which is provided in the vicinity of the magnet in the magnetic circuit configuration 72a, detects the temperature of the second force motor 72. The temperature sensor 72c then outputs to the controller 200 a signal based on the detected temperature. Thus, the second force motor 72 serves as a test force applier, which generates and applies the test force to the indenter 4 to press the indenter 4 into the surface of the sample S, the test force being generated by the electromagnetic force generated by supplying the current to the drive coil 72b positioned in the magnetic field. Furthermore, the temperature sensor 72c serves as a temperature detector, which detects the temperature of the second force motor 72.

The turret 8 includes a turret main body 8a, a rotation axis 8b rotatably pivoting the turret main boy 8a to the arm 12, and the like. By rotating the turret main body 8a, either the indenter column 5 or the objective lens 9 can be placed over the sample S. Specifically, for example, an indentation can be formed in the surface of the sample S by placing the indenter column 5 above the sample S, and the formed indentation can be observed by placing the field lenses 9 above the sample S.

The objective lens 9, which is associated with a microscope 20a of the image capturer 20, is held to a lower surface of the turret 8. When the turret 8 (turret main body 8a) is rotated to switch the objective lens 9 to a position corresponding to the image capturer 20, the objective lens 9 enables the image capturer 20 to capture an image of the sample S.

The image capturer 20 includes the microscope 20a, a CCD camera (not shown in the drawings) attached to the microscope 20a, a lighting device (not shown in the drawings) illuminating an observed position of the sample, and the like. The image capturer 20 captures an image of an indentation formed in the surface of the sample S. Then, the image capturer 20 outputs the captured image data of the indentation to the controller 200.

The display 30 is, for example, a liquid crystal display panel and performs display processing of the image of the surface of the sample S captured by the image capturer 20, various kinds of test results, and the like according to a control signal input from the controller 200. Specifically, the display 30 displays a test force adjustment button to adjust the test force, a measurement value of the electric balance 1, a measurement value of the indenter column displacement detector 63, and the like.

The operator 40 is, for example, a group of operation keys such as in a keyboard and, when operated by a user, outputs an operation signal associated with that operation to the controller 200. Moreover, the operator 40 may also include a pointing device such as a mouse or a touch screen, a remote control, and other operation devices. The operator 40 is operated when the user enters an instruction to perform a hardness test on the sample S (measurement beginning instruction), as well as when the user defines the test force applied to the indenter 4.

As shown in FIG. 2, the controller 200 includes a CPU 201, a RAM 202, and a memory 203. The controller 200 controls operation for performing a predetermined hardness test by executing a predetermined program stored in the memory 203. Furthermore, the controller 200 is connected, through a system bus, a drive circuit, and the like, to the electric balance 1, the XY stage 2, the stage lift 3, the indenter column unit 6, the pressure force applier 7, the image capturer 20, the display 30, the operator 40, and the like.

The CPU 201 retrieves a processing program stored in the memory 203, then develops and executes the processing program in the RAM 202. The CPU 61 thus performs overall control of the hardness tester 100. The RAM 202 develops a processing program executed by the CPU 201 in a program storage area within the RAM 202 and stores, in a data storage area, input data and processing results generated during execution of the processing program, and the like. The memory 203 includes, for example, a recording medium (not shown in the drawing) storing a program, data, and the like. The recording medium includes a semiconductor memory and the like. The memory 203 stores various kinds of data, various kinds of processing programs, and data processed by running the programs that allow the CPU 201 to perform overall control of the hardness tester 100. Furthermore, the memory 203 stores a test force correction table T generated based on a test force generated by the first force motor 62 or the second force motor 72, a measurement data of the test force measured by the electric balance 1, and a temperature detected by the temperature sensor 62c or the temperature sensor 72c.

In response to input of a test operation signal associated with operation for performing a hardness test in the operator 40, for example, the CPU 201 executes a predetermined program stored in the memory 203 to supply a current associated with a predetermined test force to the drive coils 62b and 72b of the first force motor 62 and the second force motor 72, respectively, based on predetermined operation conditions (for example, operation conditions for the indenter column 5) set in advance for conducting a predetermined hardness test, and thus to perform control of operations of the first force motor 62 and the second force motor 72. In addition, the CPU 201 calculates the hardness of the sample S based on an indenter column displacement signal input from the indenter column displacement detector 63. Specifically, the CPU 201 measures the hardness of the sample S based on the amount of ingress (depth of indentation) of the indenter 4 pressed into the sample S.

In addition, the CPU 201, as a test force corrector, corrects the test force generated by the first force motor 62 or the second force motor 72, based on the temperature detected by the temperature sensor 62c or the temperature sensor 72c, respectively. Specifically, the CPU 201 corrects the test force generated by the first force motor 62 or the second force motor 72, based on the test force correction table T stored in the memory 203.

Figure 3:
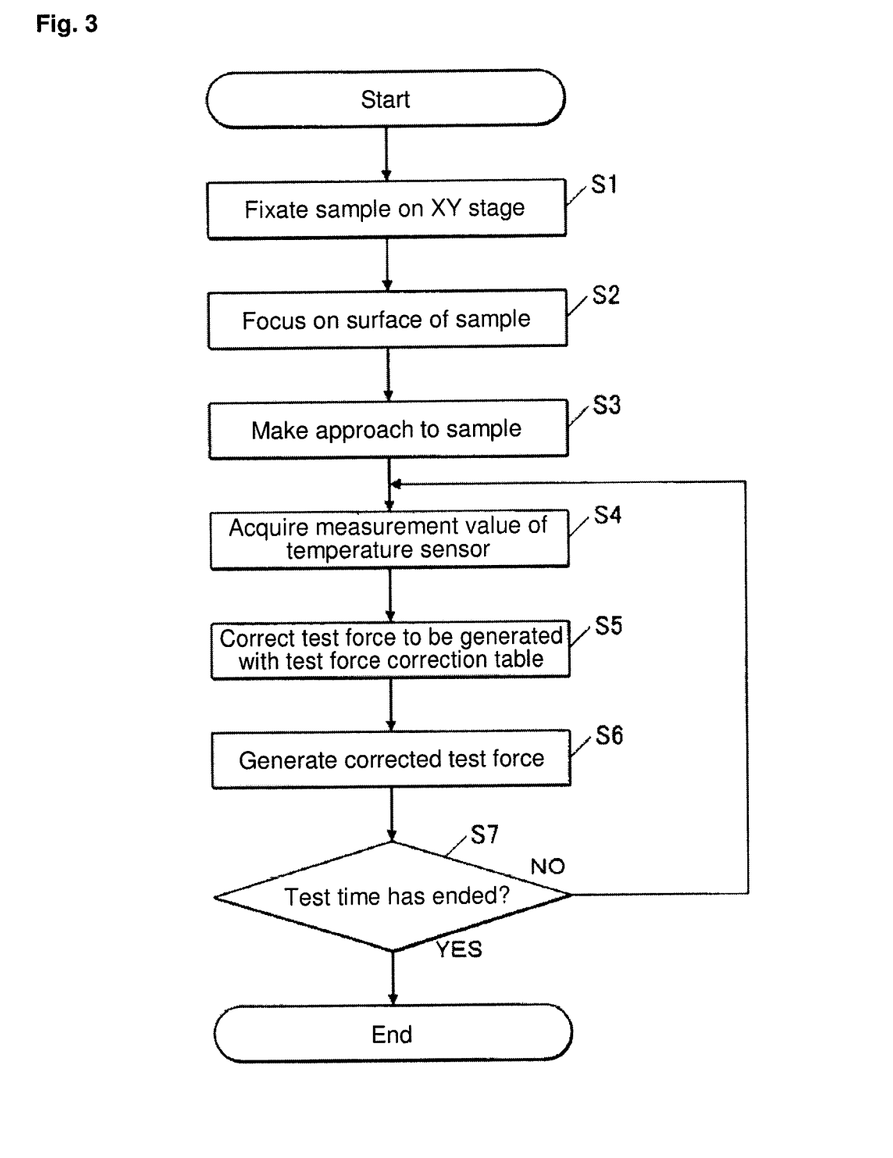
FIG. 3 is a flowchart illustrating a test force correction process in the hardness tester according to the present embodiment.

A test force correction process in the hardness tester 100 according to the present embodiment is described below with reference to a flowchart of FIG. 3. First, the sample S is fixated on the XY stage 2 (Step S1). Specifically, the user places the sample S on the upper surface of the XY stage 2 and fixates the sample S thereto. In the test force correction process, the electric balance 1 is not placed on the upper surface of the XY stage 2. Instead, the sample S is directly placed and fixated on the upper surface of the XY stage 2.

Then, the surface of the sample S is focused (Step S2). Specifically, in a state where the objective lens 9 is positioned above the sample S by rotating the turret main body 8a, the CPU 201 moves the XY stage 2 so as to position a predetermined area on the surface of the sample S directly beneath the objective lens 9. The CPU 201 then moves up and down the stage lift 3 based on image data captured by the image capturer 20 to focus on the surface of the sample S.

Then, an approach is made to the sample S (step S3). Specifically, in the state where the indenter 4 is positioned above the sample S by rotating the turret main body 8a, the CPU 201 moves the indenter 4 down toward the sample S and brings the indenter 4 into contact with the surface of the sample S.

Then, a measurement value of the temperature sensor 62c or 72c is acquired (Step S4). Specifically, the CPU 201 acquires the measurement value of the temperature sensor 62c or 72c of the first force motor 62 or the second force motor 72, respectively, which has generated a predetermined test force.

Then, the test force to be generated is corrected with reference to the test force correction table T (Step S5). Specifically, based on the temperature detected by the temperature sensor 62c or the temperature sensor 72c, respectively, in Step S4 and the test force to be generated by the first force motor 62 or the second force motor 72, the CPU 201 corrects the test force to be generated by the first force motor 62 or the second force motor 72 with reference to the test force correction table T stored in the memory 203. Thus, the CPU 201 serves as a test force corrector, which corrects the test force to be generated by the first force motor 62 or the second force motor 72, based on the temperature detected by the temperature sensor 62c or the temperature sensor 72c, respectively. A method of generating the test force correction table T will be described later with reference to FIG. 4. An example of the generated test force correction table T will be described later with reference to FIG. 5.

Then, the corrected test force is generated (Step S6). Specifically, the CPU 201 controls the first force motor 62 or the second force motor 72 to generate the test force (test force corrected in Step S5), and applies the test force to the indenter column 5. The indenter 4 provided at the lower end of the indenter column 5 then applies the test force to the sample S.

Then, whether a test time ends is determined (Step S7). Specifically, the CPU 201 determines whether a predetermined time has elapsed from generation of the test force in Step S6. When determining that the predetermined time has elapsed, the CPU 201 determines that the test time has ended (Step S7: Yes), and finishes the test force correction process. Meanwhile, when determining that the predetermined time has not elapsed, the CPU 201 determines that the test time has not ended (Step S7: No), and proceeds to Step S4 to acquire a measurement value of the temperature sensor 62c or 72c again. Thereafter, processes in Steps S4 to Step S7 are repeated until the test time ends. In the present embodiment, after the test force correction process ends (Step S7: Yes), the hardness of the sample S is calculated.

A test force correction table generation process in the hardness tester 100 according to the present embodiment is described below with reference to a flowchart of FIG. 4. First, the sample S is fixated on the XY stage 1 (Step S101). Specifically, the user places the electric balance 1 on the upper surface of the XY stage 2, and then places and fixates the sample S to the upper surface of the electric balance 1.

Then, the surface of the sample S is focused (Step S102). Specifically, in a state where the objective lens 9 is positioned above the sample S by rotating the turret main body 8a, the CPU 201 moves the XY stage 2 so as to position a predetermined area on the surface of the sample S directly beneath the objective lens 9. The CPU 201 then moves up and down the stage lift 3 based on image data captured by the image capturer 20 to focus on the surface of the sample S.

Then, an approach is made to the sample S (step S103). Specifically, in the state where the indenter 4 is positioned above the sample S by rotating the turret main body 8a, the CPU 201 moves the indenter 4 down toward the sample S and brings the indenter 4 into contact with the surface of the sample S.

Then, a height of a sample contact position is confirmed (Steps S104 and S105). Specifically, to detect the height of the sample contact position when the approach to the sample S is completed in Step S103, the CPU 201 first causes the linear encoder 52 to read the calibration mark on the scale 51 of the indenter column displacement detector 63, and then determines whether the read calibration mark on the scale 51 is positioned at 1 mm (reference position) (Step S104). When determining that the calibration mark on the scale 51 is positioned at 1 mm (Step S104: Yes), the CPU 201 proceeds to Step S106. Meanwhile, when determining that the calibration mark on the scale 51 is not positioned at 1 mm (Step S104: No), the CPU 201 causes the display 30 to display an error. Then, the CPU 201 moves up and down the stage lift 3 to adjust the height of the sample contact position (Step S105). When completing adjustment of the height of the sample contact position in Step S105, the CPU 201 proceeds to Step S104 to confirm the height of the sample contact position again.

Then, a predetermined test force is generated (Step S106). Specifically, the CPU 201 controls the first force motor 62 or the second force motor 72 to generate a predetermined test force and apply the predetermined test force to the indenter column 5. The indenter 4 provided at the lower end of the indenter column 5 then applies the test force to the sample S.

Then, the height of the sample contact position is confirmed (Steps S107 and S108). Specifically, to detect the height of the sample contact position when the predetermined test force is applied to the sample S in Step S106, the CPU 201 first causes the linear encoder 52 to read the calibration mark on the scale 51 of the indenter column displacement detector 63, and then determines whether the read calibration mark on the scale 51 is positioned at the predetermined reference position, which is at 1 mm (Step S107). When determining that the calibration mark on the scale 51 is positioned at 1 mm (Step S107: Yes), the CPU 201 proceeds to Step S109. Meanwhile, when determining that the calibration mark on the scale 51 is not positioned at 1 mm (Step S107: No), the CPU 201 causes the display 30 to display an error. Then, the CPU 201 moves up and down the stage lift 3 to adjust the height of the sample contact position (Step S108). When completing adjustment of the height of the sample contact position in Step S108, the CPU 201 proceeds to Step S107 to confirm the height of the sample contact position again. Thus, the CPU 201 serves as a determiner. Based on the amount of ingress of the indenter 4 detected by the indenter column displacement detector 63 after the indenter 4 is pressed into the surface of the sample S by the first force motor 62 or the second force motor 72, the determiner causes the stage lift 3 to adjust a height of a position where the indenter 4 comes into contact with the sample S, and determines whether the height of the position where the indenter 4 comes into contact with the sample S is at the predetermined reference position.

Then, measurement values of the electric balance 1 and the temperature sensor 62c or 72c are acquired (Step S109). Specifically, the CPU 201 acquires a measurement value of the electric balance 1 when the calibration mark on the scale 51 is positioned at 1 mm, and a measurement value of the temperature sensor 62c or 72c of the first force motor 62 or the second force motor 72, respectively, which has generated the predetermined test force in Step S106. In the present embodiment, the test force generated in Step S106 continues to be applied to the sample S at the time of Step S109 as well. Thus, the CPU 201 serves as a measurement controller. When the determiner determines that the height of the sample contact position is at the predetermined reference position (Step S107: Yes), the measurement controller causes the electric balance 1 to measure the test force applied to the sample S and causes the temperature sensor 62c or the temperature sensor 72c to detect the temperature of the first force motor 62 or the second force motor 72.

Then, a determination is made as to whether a lowering property of the magnetic density is measured (Step S110). Specifically, based on the predetermined test force generated in Step S106 and the measurement value of the electric balance 1 acquired in Step S109, the CPU 201 determines whether the lowering property of the magnetic density associated with heat generation in the magnet is measured within a predetermined period of time. When determining that the lowering property of the magnetic density is measured (Step S110: Yes), the CPU 201 proceeds to Step S111. Meanwhile, when determining that the lowering property of the magnetic density is not measured (Step S110: No), the CPU 201 causes the display 30 to display an error. Then, the CPU 201 proceeds to Step S107 to confirm the height of the sample contact position again. The lowering property of the magnetic density is not measured, for example, in a case where the measurement value of the electric balance 1 is not acquired or a case where the measurement value of the electric balance 1 is greater than the predetermined test force generated in Step S106.

Then, the test force correction table T is generated (Step S111). Specifically, the CPU 201 generates the test force correction table T from the lowering property of the magnetic density measured in Step S110 and the measurement value of the temperature sensor 62c or the temperature sensor 72c acquired in Step S109. An example is described with reference to FIG. 5, in which the test force correction table T is generated when the predetermined test force generated in Step S106 is N [kgf]. The example shown in FIG. 5 demonstrates that since the test force is reduced by 2% at a temperature of 22°, for example, the test force for a reduced amount of 2% needs to be additionally generated. Accordingly, with the test force correction table T generated in Step S111, when a predetermined test force is generated, a reduction in the reduced test force can be corrected in association with the temperature of the first force motor 62 or the second force motor 72 that generated the predetermined test force. The test force correction table T generated in Step S111 is stored in the memory 203. Thus, the CPU 201 serves as a table generator, which generates the test force correction table T based on the measurement value of the test force and the detected temperature under control of the measurement controller (Step S109).

Then, a determination is made as to whether the test force correction table T is generated for all desired test forces (Step S112). Specifically, the user displays on the display 30 the test force correction table T generated in Step S111 to determine whether the test force correction table T is generated for all desired test forces. When determining that the test force correction table T has been generated for all desired test forces (Step S112: Yes), the indenter 4 is moved to a stand-by position (Step S113) and the process ends. Meanwhile, when determining that the test force correction table T has not been generated for at least one desired test force (Step S112: No), the process proceeds to Step S106 to generate a predetermined test force (test force for which the test force correction table T has yet to be generated).

As described above, the hardness tester 100 according to the present embodiment has the test force applier (first force motor 62, second force motor 72), the temperature detector (temperature sensor 62c, temperature sensor 72c), and the test force corrector (CPU 201). The test force applier generates the test force using the electromagnetic force generated by supplying a current to the drive coil 72b provided in the magnetic field and applies the test force to the indenter 4 to press the indenter 4 into the surface of the sample S. The temperature detector detects the temperature of the test force applier. Based on the temperature detected by the temperature detector, the test force corrector corrects the test force generated from the test force applier. According to the hardness tester 100 of the present embodiment, the test force can be corrected in association with a reduction in the test force due to heat generated in the test force applier, and thus highly precise test force can be achieved.

Furthermore, the hardness tester 100 according to the present embodiment has the test force measurer (electric balance 1) and the memory (memory 203). The test force measurer measures the test force applied by the indenter 4 to the sample S placed on the upper surface. The memory stores the test force correction table T generated based on the test force generated by the test force applier, the measurement value of the test force measured by the test force measurer, and the temperature detected by the temperature detector. The test force corrector corrects the test force generated by the test force applier based on the test force correction table T stored in the memory. According to the hardness tester 100 of the present embodiment, the test force can be corrected immediately once the temperature of the test force applier is detected, and thus highly precise test force can be readily achieved.

Furthermore, the hardness tester 100 according to the present embodiment has the lifting/lowering device (lift, or stage lift 3), the ingress amount detector (indenter column displacement detector 63), the determiner (CPU 201), the measurement controller (CPU 201), and the table generator (CPU 201). The lifting/lowering device moves the test force measurer in the up-down direction. The ingress amount detector detects the amount of ingress of the indenter 4 pressed into the surface of the sample S by the test force applier. Based on the amount of ingress of the indenter 4 detected by the ingress amount detector after the indenter 4 is pressed into the surface of the sample S by the test force applier, the determiner causes the stage lift 3 to adjust the height of the position where the indenter 4 comes into contact with the sample S, and determines whether the height of the position where the indenter 4 comes into contact with the sample S is at the predetermined reference position. When the determiner determines that the height is at the predetermined reference position, the measurement controller causes the test force measurer to measure the test force applied to the sample S and causes the temperature detector to detect the temperature of the test force applier. The table generator generates the test force correction table T based on the measurement value of the test force and the detected temperature under control of the measurement controller. According to the hardness tester 100 of the present embodiment, the test force correction table T is generated when the height of the position where the indenter 4 comes into contact with the sample S is at the predetermined reference position, specifically, when the indenter 4 is situated in a position where the test force is most effectively transmitted to the sample S. This minimizes a reduction in the test force associated with heat generated in the test force applier as well as a correction amount of the test force.

A concrete description was given based on an embodiment according to the present disclosure. However, the present invention is not limited to the above-described embodiment and may be modified within a scope not deviating from the substance of the invention.

Figure 4:
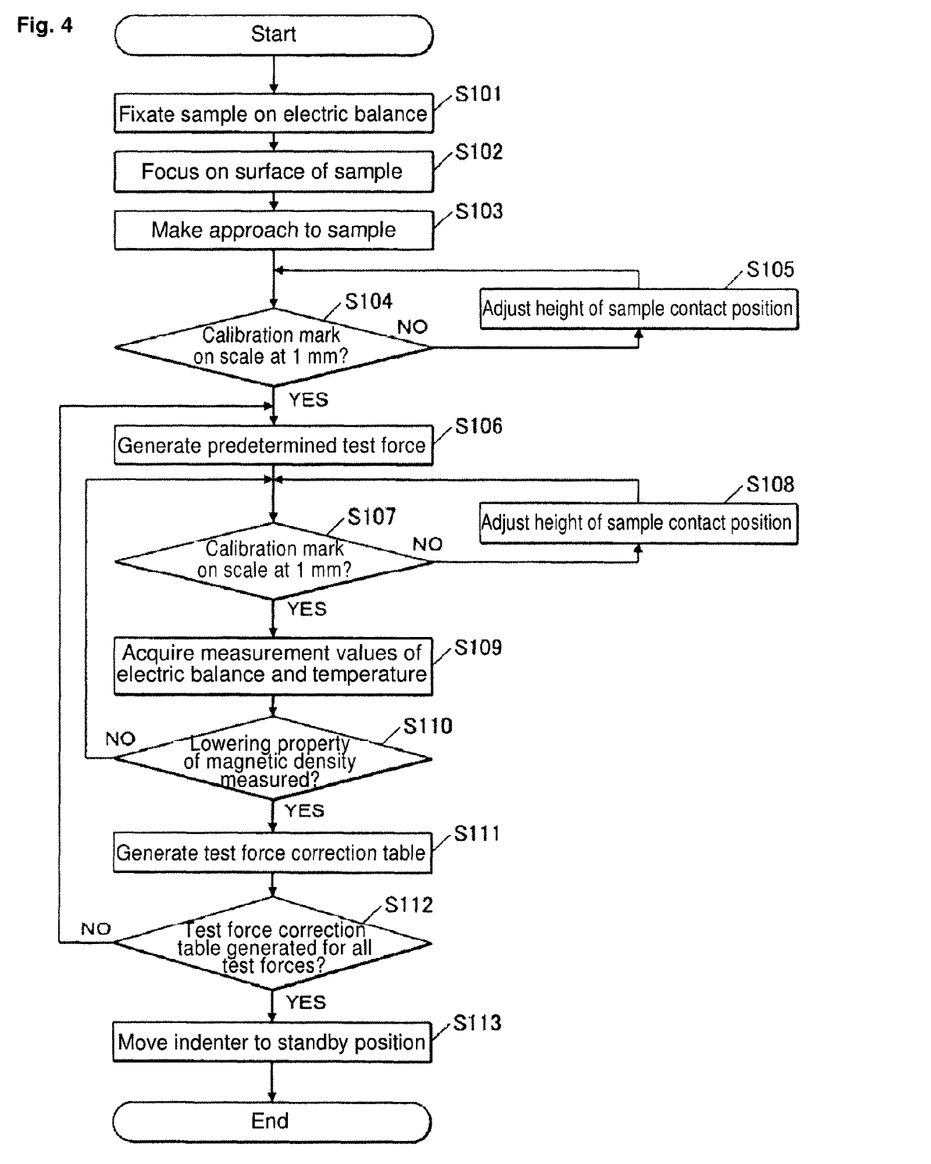
FIG. 4 is a flowchart illustrating a test force correction table generation process in the hardness tester according to the present embodiment.
Figure 5:
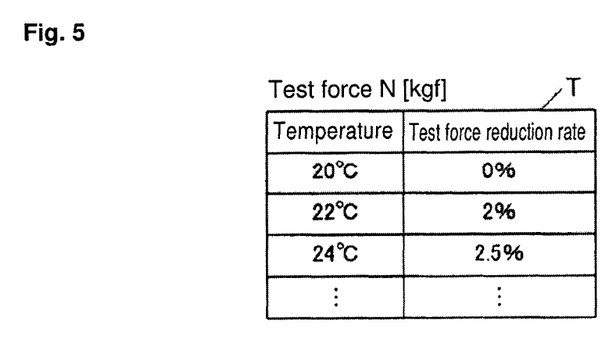
FIG. 5 illustrates an exemplary test force correction table.

In the embodiment above, for example, the stage lift 3 is automatically moved up and down to adjust the height of the sample contact position (Steps S105 and S108 in FIG. 4). However, the present invention is not limited to this. For example, the stage lift 3 may be manually moved up and down to allow a user to manually adjust the height.

Furthermore, in the embodiment above, when the read calibration mark on the scale 51 is determined not to be positioned at 1 mm (reference position) during confirmation of the height of the sample contact position (Steps S104 and S107 in FIG. 4: No), an error is displayed on the display 30. However, the present invention is not limited to this. For example, a speaker capable of outputting audio may be provided to output an alarm sound, instead of the error on the display 30. Alternatively, the alarm sound may be output along with the error on the display 30.

Furthermore, in the embodiment above, when the lowering property of the magnetic density is determined not to be measured within a predetermined period of time (Step S110 in FIG. 4: No), an error is displayed on the display 30. However, the present invention is not limited to this. For example, an alarm sound may be output instead of the error on the display 30, or an alarm sound may be output along with the error on the display 30. In addition, after the error is displayed on the display 30, the process proceeds to Step S107 to confirm the height of the sample contact position again. However, the present invention is not limited to this. For example, the process may proceed to Step S106 to generate a predetermined test force again, or to Step S103 to make an approach to the sample S again.

Furthermore, in the embodiment above, two force motors (the first force motor 62 and the second force motor 72) are provided as the test force applier. However, the present invention is not limited to this. For example, only either of the first force motor 62 or the second force motor 72 may be provided.

Furthermore, in the embodiment above, the test force correction table T is generated in the test force correction table generation process shown in FIG. 4. However, the present invention is not limited to this. For example, based on the lowering property of the magnetic density statistically obtained from a plurality of hardness testers 100, a generic test force correction table T may be prepared in advance and stored in the memory 203.

Furthermore, in the embodiment above, the test force correction table T is generated and the test force is corrected with reference to the test force correction table T. However, the present invention is not limited to this. For example, based on the lowering property of the magnetic density statistically obtained from a plurality of hardness testers 100, a predetermined calculation formula may be developed representing a relation between a temperature and a reduction in test force. Then, the test force may be corrected based on the developed calculation formula.

In addition, within a scope not deviating from the substance of the present invention, appropriate modifications may also be made to detailed structures and operations of each component configuring the hardness tester 100.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular structures, materials and embodiments, the present invention is not intended to be limited to the particulars disclosed herein; rather, the present invention extends to all functionally equivalent structures, methods and uses, such as are within the scope of the appended claims.

The present invention is not limited to the above-described embodiments, and various variations and modifications may be possible without departing from the scope of the present invention.

What is claimed is:

1. A hardness tester for measuring hardness of a sample by applying a test force to a surface of the sample with an indenter to form an indentation and by measuring a depth of indentation of the indenter at a time of forming the indentation, the hardness tester comprising:
   a test force applier configured to generate the test force using an electromagnetic force generated by supplying a current to a drive coil provided in a magnetic field, the test force applier further configured to apply the test force to the indenter to press the indenter into the surface of the sample;
   a temperature detector configured to detect a temperature of the test force applier; and
   a test force corrector configured to correct the test force generated from the test force applier by a predetermined value, based on the temperature detected by the temperature detector.

2. The hardness tester according to claim 1, further comprising:
   a test force measurer configured to measure the test force applied by the indenter to the sample placed on an upper surface; and
   a memory configured to store a test force correction table generated based on the test force generated by the test force applier, a measurement value of the test force measured by the test force measurer, and the temperature detected by the temperature detector, wherein the test force corrector is further configured to correct the test force generated by the test force applier based on the test force correction table stored in the memory.

3. The hardness tester according to claim 2, further comprising:

a lift configured to move the test force measurer in an up-down direction;

an ingress amount detector configured to detect an amount of ingress of the indenter pressed into the surface of the sample by the test force applier;

a determiner configured to cause the lift to adjust a height of a position where the indenter comes into contact with the sample based on the amount of ingress of the indenter detected by the ingress amount detector after the indenter is pressed into the surface of the sample by the test force applier, the determiner further configured to determine whether the height of the position where the indenter comes into contact with the sample is at a predetermined reference position;

a measurement controller configured to cause the test force measurer to measure the test force applied to the sample, the measurement controller further configured to cause the temperature detector to detect the temperature of the test force applier when the determiner determines that the height is at the predetermined reference position; and a table generator configured to generate the test force correction table based on a measurement value of the test force and the detected temperature under control of the measurement controller.

* * * * *